United States Patent [19]

Di Bella

[11] 4,202,844

[45] May 13, 1980

[54] PROCESS FOR THE PRODUCTION OF ORGANIC PHOSPHATES

[75] Inventor: Eugene P. Di Bella, Piscataway, N.J.

[73] Assignee: Tenneco Chemicals, Inc., Saddle Brook, N.J.

[21] Appl. No.: 930,445

[22] Filed: Aug. 2, 1978

[51] Int. Cl.$^2$ ............................................. C07F 9/09
[52] U.S. Cl. ................................................... 260/985
[58] Field of Search ........................................ 260/985

[56] References Cited

U.S. PATENT DOCUMENTS 3,144,302  8/1964  Fielding ........................... 260/985 X Primary Examiner—Anton H. Sutto
Attorney, Agent, or Firm—Evelyn Berlow

[57] ABSTRACT

Organic phosphates are prepared in good yields by contacting the corresponding organic phosphite with an oxygen-containing gas that is preferably oxygen in the presence of a catalyst that comprises nitrogen dioxide in amounts that will provide at least 0.40 mole of oxygen and from 0.01 mole to 0.25 mole of nitrogen dioxide catalyst per mole of phosphite at a temperature in the range of −30° C. to 120° C.

9 Claims, No Drawings

PROCESS FOR THE PRODUCTION OF ORGANIC PHOSPHATES

This invention relates to a process for the production of organic phosphates. More particularly, it relates to a process for the production of organic phosphates by the nitrogen dioxide-catalyzed oxygenation of the corresponding phosphites.

A number of processes for the production of organic phosphates by the oxidation of organic phosphites have been reported. Processes that employ such oxidizing agents as hydrogen peroxide, peracids, epoxides, nitrogen oxides, sulfur trioxide, or ozone as the oxidizing agent have generally proven unsatisfactory for the commercial production of organic phosphates because they do not give high yields of the phosphates, because they produce substantial amounts of hydrolyzed phosphates and other undesirable reaction products, and because they require the use of costly reagents and processing procedures. A review of these and other processes for the oxidation of organic phosphites to phosphates appears in "Organic Phosphorus Compounds", Volume 6, by G. M. Kosolapoff and L. Maier (New York: John Wiley and Sons, 1973), page 247 ff.

Processes in which organic phosphites are oxidized with oxygen in the presence of catalysts have also been reported. Baranauckas et al. disclosed processes in which phosphites were oxidized by contacting them with oxygen in the presence of a catalyst that is copper, a transition metal, or an oxide of copper or a transition metal (U.S. Pat. No. 3,333,030) or a catalyst that is aluminum oxide or vanadium pentoxide (U.S. Pat. No. 3,136,805). Heckenbleikner et al. disclosed processes for the preparation of trialkyl and trialkenyl phosphates by oxidation of the corresponding phosphite with oxygen or an oxygen-containing gas in the presence of a catalyst that is a transition metal carboxylate (U.S. Pat. No. 3,939,229) or in the presence of a source of free radicals, e.g., an organic peroxide or an azo compound, and in the presence of a light of wavelength of 2000 to 4000 A (U.S. Pat. No. 3,923,620). A process in which organic phosphites are oxidized using oxygen and a peroxide catalyst was disclosed by Nehmsmann et al. in U.S. Pat. No. 3,277,217. While these processes give good results when trialkyl or trialkenyl phosphites are the starting materials, they usually require lengthy reaction periods for the conversion of triaryl phosphites to triaryl phosphates. In addition, they may require high temperatures and precise control of reaction conditions if satisfactory yields are to be obtained, they may require the use of costly reactants, and they form products that contain catalyst and other impurities that must be removed before the products can be used, for example, as plasticizers, lubricant additives, or flame-retardants.

A process for the oxidation of organic phosphites to organic phosphates using stoichiometric quantities of dinitrogen tetroxide at $-78°$ to $0°$ C. in a solvent was reported by Cox et al. (J. Am. Chem. Soc. 80, 5441 (1958) to give a mixture of nitrous oxide and nitrogen as reaction by-products. Kuhn et al. (J. Am. Chem. Soc. 82, 4792 (1960)) oxidized triethyl phosphite to triethyl phosphate using nitric oxide as the oxidant and obtained nitrous oxide as the reduction product. Since neither nitrous oxide nor nitrogen is reoxidizable to nitric oxide and/or nitrogen dioxide except under extreme conditions, the teachings of these references would seem to preclude a nitrogen dioxide-catalyzed oxygenation of organic phosphites to phosphates that is based on the reoxidation of the reduced nitrogen oxide(s) to nitrogen dioxide and/or nitric oxide.

In accordance with this invention, it has been found that organic phosphates can be prepared in high yields by the nitrogen dioxide-catalyzed oxygenation of the corresponding organic phosphites. This process provides a low-cost, efficient procedure for the production of organic phosphates and particularly for the production of triaryl phosphates.

In the process of this invention, organic phosphites are oxidized to the corresponding phosphates by contacting them with oxygen in the presence of a catalyst that comprises nitrogen dioxide. The preferred catalyst is the commercially-available nitrogen dioxide/dinitrogen tetroxide equilibrium mixture. Alternatively, the catalyst may be a nitrogen oxide, such as nitric oxide (NO) and dinitrogen trioxide ($N_2O_3$), that can be oxidized with molecular oxygen to nitrogen dioxide or to the nitrogen dioxide/dinitrogen tetroxide equilibrium mixture. In this process, the reduction of nitrogen dioxide/dinitrogen tetroxide proceeds stepwise via nitric oxide to, ultimately, nitrous oxide, but in the presence of molecular oxygen, the intermediate nitric oxide is intercepted for reoxidation to nitrogen dioxide, which is reused as the oxidation catalyst. This oxidative interception which apparently occurs to a significant extent allows catalytic use of nitrogen dioxide/dinitrogen tetroxide in a phosphite-oxygenation system. The reaction scheme operating in the nitrogen dioxide-catalyzed oxygenzation of organic phosphites to the corresponding organic phosphate by the process of this invention appears to be as follows:

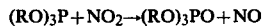

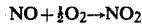

In the process of this invention, an organic phosphite is contacted with an oxygen-containing gas, which is preferably oxygen, in the presence of a nitrogen dioxide catalyst at a temperature in the range of $-30°$ C. to $120°$ C., preferably in the range of $0°$ to $60°$ C. Particularly good results have been obtained when the oxidation was carried out at a temperature in the range of $25°$ C. to $55°$ C.

The addition of the oxygen-containing gas to the phosphite is continued until sufficient oxygen has been added for the quantitative conversion of the phosphite to phosphate. In open systems in which the reaction mixture is sparged with the oxygen-containing gas, the addition of the gas, which is at an oxygen pressure of at least 0.05 atmosphere, is continued until at least 0.40 mole of oxygen and preferably at least 0.5 mole of oxygen per mole of phosphite has been added. When the oxidation is carried out in an autoclave or another closed system, sufficient oxygen or oxygen-containing gas is added to maintain a pressure in the range of 1.5 to 10 atmospheres at a rate that is substantially equivalent to that at which it is being consumed by the reaction. An excess of oxygen may be present during the oxidation reaction. In most cases, the amount of oxgen that is added to the phosphite is from 100% to 3000% of the stoichiometric amount required for the oxidation, with most favorable results being obtained when from 300% to 800% of the stoichiometric amount of oxygen is used.

The amount of catalyst that is used is that which will provide from 0.01 mole to 0.25 mole of $NO_2$ per mole of phosphite, with a catalyst level of 0.05 mole to 0.15 mole of NO$_2$ per mole of phosphite preferred. Quantitative conversions of the phosphite to phosphate have resulted when 0.10 mole to 0.12 mole of NO$_2$ was used per mole of phosphite. All of the catalyst may be present at the start of the reaction, or it may be added incrementally during the course of the oxygenation reaction.

The oxidation of the phosphites may be carried out in a solvent medium, but the use of a solvent medium is not essential. The solvents that can be used are inexpensive volatile liquids that are resistant to oxidation and other reactions with nitrogen oxides, for example, halogenated aliphatic hydrocarbons and aromatic hydrocarbons.

During the catalyzed oxygenation of the phosphites, the reaction mixture should be agitated efficiently to insure adequate contact between the phosphite and the gaseous reactants.

The process of this invention may be carried out in the presence of ultraviolet light, but light is not necessary for its efficient operation.

The NO$_2$-catalyzed oxygenation process may be carried out under atmospheric, subatmospheric, or superatmospheric pressure in a batchwise, semi-continuous, or continuous manner.

A wide variety of organic phosphites can be converted to the corresponding phosphates by the process of this invention. These include alkyl, aryl, alkaryl, and aralkyl phosphites that have the structural formula

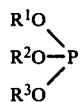

wherein $R^1$, $R^2$, and $R^3$ each represents an alkyl or haloalkyl group having 1 to 18 carbon atoms, an alkoxyalkyl group having 2 to 18 carbon atoms, an aryl or haloaryl group having 6 to 18 carbon atoms, or an alkoxyaryl, alkaryl, or aralkyl group having 7 to 18 carbon atoms. Illustrative of these phosphites are the following: trimethyl phosphite, triethyl phosphite, tri-tert-butyl phosphite, tri-n-hexyl phosphite, tridecyl phosphite, triodecyl phosphite, trioctadecyl phosphite, methyl didecyl phosphite, diethyl dodecyl phosphite, tri(chloroethyl)phosphite, tri(bromohexyl)phosphite, tri(ethoxybutyl)phosphite, tri(butoxyoctyl)phosphite, triphenyl phosphite, tricresyl phosphite, trixylyl phosphite, 2,4-dichlorophenyl dinonyl phosphite, di(p-methoxyphenyl) dodecyl phosphite, phenyl di(2-chloroethyl)Phosphite, di(p-bromophenyl)diodecyl phosphite, cresyl di(2-tetradecylphenyl) phosphite, tribenzyl phosphite, bromohexyl phosphite, tri(2-napthyl) phosphite, tri(2-phenylphenyl)phosphite, and mixtures thereof. The process of this invention is particularly well suited to the oxidation of triaryl phosphites, such as triphenyl phosphite, tri(alkylphenyl) phosphites, and phenyl alkylphenyl phosphites, that react very slowly under the conditions reported in the literature for other oxidation processes.

When the oxidation of the organic phosphite has been completed, the reaction mixture may be heated under subatmospheric pressure to separate the solvent and residual gases from the product. The product may be further purified, for example, by distillation or crystallization.

The invention is further illustrated by the following examples.

EXAMPLE 1

To a three-necked vessel equipped with stirrer, thermometer, addition funnel, and gas sparge tube was charged 155.1 grams (0.50 mole) of triphenyl phosphite. While the triphenyl phosphite was being agitated, continuously sparged with oxygen at the rate of 400 ml. per minute, and maintained at 25°–30° C., there was added to it over a period of 3 hours a solution of 2.6 grams (0.0565 mole) of nitrogen dioxide (NO$_2$/N$_2$O$_4$ equilibrium mixture) in 80 grams of carbon tetrachloride. External cooling was required to maintain the reaction mixture at 25°–30° C. After the addition of the nitrogen dioxide solution had been completed, the reaction mixture was sparged with oxygen for one hour and then heated to 80° C./1 mm to remove solvent and residual gases from it.

There was obtained 163.9 grams of an amber oil that solidified on standing at ambient temperature. The product was shown by gas chromatographic analysis to contain 99.4% by weight of triphenyl phosphate and 0.6% by weight of phenol.

EXAMPLE 2

Using the procedure described in Example 1, a series of runs in which the reaction conditions were varied was carried out. In each case, 5.85 moles of oxygen per mole of phosphite was supplied during the addition of the nitrogen dioxide solution. The reaction conditions employed and the results obtained are summarized in Table I.

Table I

| | NO$_2$-Catalyzed Oxidation of Triphenyl Phosphite | | | | | | |
|---|---|---|---|---|---|---|---|
| Example No. | 2A | 2B | 2C | 2D | 2E | 2F | 2G |
| Weight of NO$_2$ Added (g) | 1.3 | 1.3 | 2.6 | 2.6 | 2.6 | 2.6 | None |
| Mole Ratio NO$_2$/P | 0.056 | 0.056 | 0.113 | 0.113 | 0.113 | 0.113 | — |
| Exposure to Light | Exposed to UV Light | Exposed to UV Light | Exposed to UV Light | Exposed to UV Light | Exposed to Ambient Light | None | Exposed to Ambient Light |
| Temperature (°C.) | 0–10 | 25–30 | 0–10 | 25–30 | 25–30 | 25–30 | 20–25 |
| Weight of Product (g) | 159.0 | 169.2 | 162.8 | 162.5 | 163.9 | 163.1 | 155.5 |
| Composition of Product (%) | | | | | | | |
| Phenol | 1.8 | 7.0 | 3.2 | 4.2 | 0.6 | 0.7 | 0.5 |
| Phosphite | 57.1 | 43.6 | 13.7 | 8.2 | 0 | 0.1 | 99.5 |
| Phosphate | 41.1 | 49.4 | 80.1 | 87.6 | 99.4 | 99.2 | 0 |
| Yield of Phosphate (%) | 40.0 | 46.3 | 79.8 | 87.1 | 99.6 | 99.2 | 0 |

From the data in Table I, it will be seen that the reaction does not require ultraviolet photoinitiation.

EXAMPLE 3

A. To a mixture of 3005 grams (32 moles) of phenol, 60 grams of acid clay (Filtrol-13), and 6 grams of p-toluene-sulfonic acid was added 625 grams (14.9 moles) of propylene over a period of 8 hours during which the reaction mixture was efficiently stirred and maintained at 130°-135° C. Following a post-heating period of 3 hours at 180° C. to effect disproportionation/isomerization to a composition low in ortho substitution, the reaction mixture was cooled to 90° C. and filtered.

There was obtained 3570 grams of an isopropylphenol/phenol product (98.4% yield) having the following composition: phenol, 49.9%; o-isopropylphenol, 20.6%; m- and p-isopropylphenols, 21.9%; 2,6-diisopropylphenol, 0.9%; other diisopropylphenols, 6.6%; and 2,4,6-triisopropylphenol, 0.1%.

To this isopropylphenol/phenol mixture was added 1375 grams (10 moles) of phosphorus trichloride over a period of 6 hours while the reaction mixture was efficiently stirred and maintained at 60°-65° C. and hydrogen chloride was evolved steadily. After the reaction mixture had been heated at 220° C. for 2 hours to complete the removal of 1116 grams of hydrogen chloride and other volatile compounds from it, it was cooled to 170° C. and vacuum was applied gradually to remove the last traces of hydrogen chloride. The reaction was then heated at 170°-175° C./1 mm to distill 289 grams of phenolic compounds from it. The residue was cooled to 90°-95° C., stirred with a mixture of 20 grams of sodium carbonate, 20 grams of clay acid (Attasorb LVM), and 20 grams of filter-aid (Celite 535) at this temperature for 1 hour, and filtered.

There was obtained in 94% yield an isopropylphenyl/phenyl phosphite composition that had an acid number of 0.01, specific gravity at 25° C. of 1.117, and viscosity at 25° C. of 37.6 centistokes and that contained 50 ppm of labile chlorine.

B. Using the procedure described in Example 1, the isopropylphenyl/phenyl phosphite was oxidized under varying reaction conditions. The conditions employed and the results obtained are summarized in Table II.

Table II

NO$_2$-Catalyzed Oxidation of Isopropyl-phenyl/Phenyl Phosphite in Open Systems
(Gas Sparging at Pressure of 1 Atmosphere)

| Example No. | 3A | 3B | 3C | 3D |
|---|---|---|---|---|
| Batch Size (Moles Phosphite) | 1.00 | 0.30 | 0.50 | 0.50 |
| Mole Ratio NO$_2$/P | 0.100 | 0.113 | 0.113 | 0.113 |
| Oxygen Flow Rate (ml/min.) | 200 | 400 | 400 | 400 |
| Moles O$_2$/mole P/Hr. | 0.49 | 3.32 | 1.95 | 1.95 |
| Exposure to Light | None | Exposed to UV Light | None | None |
| Temperature (°C.) | 25-30 | 0-10 | 25-30 | 50-55 |
| Weight of Product (g) | 379.0 | 113.4 | 189.9 | 190.8 |
| Composition of Product (%) | | | | |
| Phenol | 0.4 | 0.9 | 0.2 | 0.4 |
| Phosphite | 24.3 | 27.7 | 19.3 | 17.1 |
| Phosphate | 75.3 | 71.4 | 80.5 | 82.5 |
| Yield of Phosphate (%) | 74.2 | 70.2 | 79.5 | 81.9 |

EXAMPLE 4

The isopropylphenyl/phenyl phosphite whose preparation is described in Example 3A, was oxidized in closed systems under varying reaction conditions. The conditions employed and the results obtained are summarized in Table III.

Table III

NO$_2$-Catalyzed Oxidation of Isopropyl-phenyl/phenyl Phosphite in Closed Systems

| Example No. | 4A | 4B | 4C |
|---|---|---|---|
| Batch Size (Moles Phosphite) | 0.50 | 0.50 | 0.75 |
| Mole Ratio NO$_2$/P | 0.091 | 0.113 | 0.113 |
| Temperature (°C.) | 25-30 | 25-30 | 35-40 |
| Processing Conditions | Head space oxygen at 29-30 psia; No sparge | In Parr Shaker at 10-25 psig O$_2$ with incremental injection of NO$_2$ in C Cl$_4$ solution | In Parr Autoclave at 45-50 psig O$_2$ |
| Weight of Product (g) | 186.7 | 189.9 | 287.1 |
| Composition of Product (%) | | | |
| Phenol | 0.4 | 0.3 | 0.2 |
| Phosphite | 73.3 | 19.5 | — |
| Phosphate | 26.3 | 80.2 | 99.8 |
| Yield of Phosphate (%) | 22.4 | 79.4 | 99.5 |

EXAMPLE 5

Using the procedure described in Example 1, diphenyl isodecyl phosphite was sparged with oxygen at the rate of 400 ml/min/mole of phosphite for 6 hours at 25° C. and 1 atmosphere pressure while a solution of nitrogen dioxide (NO$_2$/N$_2$O$_4$ equilibrium mixture) in carbon tetrachloride was added to it. The amount of oxygen added was 5.9 moles O$_2$/mole phosphite, and the amount of nitrogen dioxide added was 0.50 mole NO$_2$/mole phosphite. A quantitative conversion of the phosphite to diphenyl isodecyl phosphate was effected.

EXAMPLE 6

Using the procedure described in Example 5, triethyl phosphite was oxidized to triethyl phosphate. The amount of oxygen used was 5.9 moles O$_2$/mole phosphite, and the amount of nitrogen dioxide used was 0.113 mole/mole phosphite. A 60% yield of triethyl phosphate was obtained.

EXAMPLE 7

Using the procedure described in Example 5, tris(2-chloroethyl) phosphite was oxidized to tris(2-chloroethyl) phosphate. The amount of oxygen used was 5.9 moles O$_2$/mole phosphite, and the amount of nitrogen dioxide used was 0.113 mole/mole phosphite. A 35% of the phosphate was obtained.

EXAMPLE 8

Using the procedure described in Example 1, but using, instead of oxygen, dry air at a flow rate of 800 ml/minute, which corresponds over the 3-hour NO$_2$-addition period to the addition of 2.46 moles O$_2$/mole phosphite, there was obtained 159 grams of a product that contained 46.4% by weight of triphenyl phosphate, 49/8% by weight of triphenyl phosphite, and 3.9% by weight of phenol. The yield of triphenyl phosphate was 44.9%.

COMPARATIVE EXAMPLE A

Using the procedure described in Example 1, but sparging with nitrogen instead of oxygen, the yield of triphenyl phosphate was 22%.

Comparison of the results obtained in Examples 1 and 8 and Comparative Example A shows that both oxygen and air effect oxidation of triphenyl phosphite in addition to that contributed by the nitrogen dioxide.

COMPARATIVE EXAMPLE B

To further define the role of nitrogen dioxide in this system, 103.4 grams (0.333 mole) of triphenyl phosphite was sparged with nitrogen and maintained at 15°–20° C. over a three hour period while 5.5 grams (0.12 mole) of nitrogen dioxide in 80 grams of carbon tetrachloride was added to it. External cooling was used to maintain the reaction mixture at 15°–20° C. The reaction mixture was heated to 80° C./1 mm to remove solvent and residual gases from it.

There was obtained 107.5 grams of a product that contained 61.9% by weight of triphenyl phosphate, 31.5% by weight of triphenyl phosphite, and 6.6% by weight of phenol. The yield of triphenyl phosphate was 62.1%.

The product of the reduction of nitrogen dioxide in this process was principally nitrous oxide.

COMPARATIVE EXAMPLE C

When the procedure described in Comparative Example B was repeated but nitric oxide in the amount of 4 moles NO/mole phosphite was used as the sole oxidant, a 22% yield of triphenyl phosphate was obtained.

COMPARATIVE EXAMPLE D

When the procedure described in Comparative Example B was repeated but nitrous oxide in the amount of 1.27 moles $N_2O$/mole phosphite was used as the sole oxidant, a 1% yield of triphenyl phosphate was obtained.

From the data in Comparative Examples B, C and D, it will be seen that nitrogen dioxide and nitric oxide, which is a by-product of the reaction of triphenyl phosphite with nitrogen dioxide, can act as oxidants for triphenyl phosphite in the absence of oxygen and that the oxidation of triphenyl phosphite is not effected to any significant degree by nitrous oxide.

What is claimed is:

1. The process for the production of organic phosphates that comprises contacting an organic phosphite having the structural formula

wherein $R^1$, $R^2$, and $R^3$ each represents an alkyl or haloalkyl group having 1 to 18 carbon atoms, an alkoxyalkyl group having 2 to 18 carbon atoms, an aryl or haloaryl group having 6 to 18 carbon atoms, or an alkoxyaryl, alkaryl, or aralkyl group having 7 to 18 carbon atoms with an amount of an oxygen-containing gas that will provide at least 0.40 mole of oxygen per mole of said phosphite in the presence of an amount of a nitrogen dioxide catalyst that will provide 0.01 mole to 0.25 mole of nitrogen dioxide per mole of said phosphite at a temperature in the range of −30° C. to 100° C.

2. The process of claim 1 wherein the oxygen-containing gas is oxygen.

3. The process of claim 1 wherein the catalyst is a nitrogen dioxide/dinitrogen tetroxide equilibrium mixture.

4. The process of claim 1 wherein the phosphite is contacted with oxygen in the amount of at least 0.50 mole per mole of phosphite.

5. The process of claim 1 wherein the amount of catalyst used is that which will provide 0.10 mole to 0.12 mole of nitrogen dioxide per mole of phosphite.

6. The process of claim 1 wherein the organic phosphite is triphenyl phosphite.

7. The process of claim 1 wherein the organic phosphite is isopropylphenyl/phenyl phosphite.

8. The process of claim 1 wherein the organic phosphite is contacted with an oxygen-containing gas and the $NO_2$ catalyst at an oxygen pressure of at least 0.05 atmosphere.

9. The process of claim 1 wherein the organic phosphite is contacted with oxygen and the $NO_2$ catalyst at a pressure in the range of 1.5 atmospheres to 10 atmospheres.

* * * * *